United States Patent [19]

Paap

[11] 4,289,020
[45] Sep. 15, 1981

[54] MICROWAVE-GAMMA RAY WATER IN CRUDE MONITOR

[75] Inventor: Hans J. Paap, Houston, Tex.

[73] Assignee: Texaco Inc., White Plains, N.Y.

[21] Appl. No.: 106,584

[22] Filed: Dec. 26, 1979

[51] Int. Cl.$^3$ ............................................ G01N 22/00
[52] U.S. Cl. .................................. 73/61.1 R; 250/301
[58] Field of Search .............. 73/61.1 R, 53; 250/301, 250/272, 273, 274

[56] References Cited

U.S. PATENT DOCUMENTS 3,246,145  4/1966  Higgins ........................... 250/301 X
3,498,112  3/1970  Howard ............................ 73/61.1 R

*Primary Examiner*—Gerald Goldberg
*Assistant Examiner*—Joseph W. Roskos

*Attorney, Agent, or Firm*—Carl G. Ries; Robert A. Kulason; Ronald G. Gillespie

[57] ABSTRACT

A microwave-gamma ray water-in-crude monitor measures the percent quantity of water in crude oil flowing in a pipe line by causing the crude oil to flow through a measuring cell. A microwave transmitter and a gamma ray source are arranged with the measuring cell and transmits microwave energy and gamma rays through the measuring cell. A microwave receiver and a gamma ray detector receive the energies transmitted through the measuring cell and provides signals in accordance with the received energies. Apparatus connected to the microwave receiver and to the gamma ray detector provide a display of the water content of the crude oil in accordance with the signals from the microwave receiver and the gamma ray detector.

10 Claims, 3 Drawing Figures

4,289,020

MICROWAVE-GAMMA RAY WATER IN CRUDE MONITOR

BACKGROUND OF THE INVENTION

Field of the Invention

The present invention relates to monitors in general and, more particularly, to a water-in-crude monitor.

SUMMARY OF THE INVENTION

A microwave-gamma ray water-in-crude monitoring system measures the percent quantity of fresh water or salt water in crude oil flowing in a pipe line. The system includes a measuring cell arranged with the pipe line so that the crude oil flows through the measuring cell. A microwave transmitter subsystem and a gamma ray source are arranged with the measuring cell so that microwave energy and gamma rays are transmitted through the measuring cell. A microwave receiving subsystem and a gamma ray detector provide signals corresponding to received microwave energy and to the received gamma rays, respectively. Apparatus connected to the microwave receiver and to the gamma ray detector provides an indication of the percentage of water in the crude oil.

The objects and advantages of the invention will appear more fully hereinafter from a consideration of the detailed description which follows, taken together with the accompanying drawings which follow, wherein one embodiment of the invention is illustrated by way of example. It is to be expressly understood, however, that the drawings are for illustration purposes only and are not to be construed as defining the limits of the invention.

DESCRIPTION OF THE INVENTION

A method of determining the fresh water or salt water content of flowing streams of gas free crude oil under the conditions encountered in well flow lines utilizes the measurement of microwave attenuation caused by water present in the crude stream. Dielectric relaxation of the water molecules at microwave frequencies causes severe attenuation of electromagnetic waves of centimeter wavelength. Attenuation of centimeter waves has been used to measure moisture content in many materials such as concrete and core slabs, see "Microwave Attenuation—A New Tool for Monitoring Saturations in Laboratory Flooding Experiments," by R. W. Parsons, Marathon Oil Company, Society of Petroleum Engineers Journal, August 1975, pp. 302–310.

The propagation of a plane-parallel electromagnetic wave can be respresented by the following equations:

$$E = E_o e^{-\alpha x} \cdot e^{j2\pi(\nu t - \beta x/2\pi)} \quad (1)$$

$$H = H_o e^{-\alpha x} \cdot e^{j2\pi(\nu t - \beta x/2\pi)} \quad (2)$$

where E and H are the electric and magnetic field vectors, x and t the direction of propagation and propagation time in space and $\nu$ the frequency of the wave. Obviously the wave has a time period $T = 1/\nu$ and a space period $\lambda = 2\pi/\beta$ (wavelength). Also the wave is attenuated by the factor $e^{-\alpha x}$ as it proceeds along the x-direction. The attenuation factor $\alpha$ is a function of dielectric and magnetic characteristics of the propagating material at the frequency of the wave and is of interest only to the water-in-crude determination. Assuming no magnetic losses in the propagating materials which is certainly true for crude streams, the attenuation factor is given by the following equation:

$$\alpha = (2\pi/\lambda_o)\{(K'/2)[(1 + (K''/K')^2)^{\frac{1}{2}} - 1]\}^{\frac{1}{2}} \quad (3)$$

where
$\lambda_o$ = wavelength in empty space (air),
$k'$ = relative dielectric constant, and
$k''$ = relative loss factor.

Figure 1:
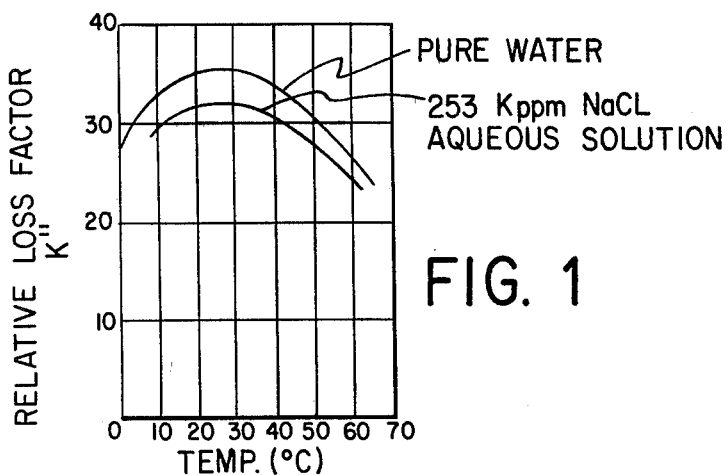
FIG. 1 is a plot of relative loss factor versus temperature at a particular wavelength.

The parameters $k'$ and $k''$ are dependent on the frequency of the wave, the temperature and the material composition of the propagating material. The hydrocarbons in crude oils have low values of $k'$ and $k''$ in comparison of those of water and aqueous solutions of sodium chloride. As an example $k''$, the relative loss factor, for pure water and for a 253 kppm aqueous NaCl solution is plotted versus temperature for a wavelength of 1.267 cm (23.68 GHz) in FIG. 1. Data for the plot was obtained from "The Dielectric Properties of Water in Solutions" by J. B. Hasted, S. M. M. El Sabeh, Transaction of the Faraday Society, V. 49, 1953, London. Note that the loss factor has a maximum at about 28° C. This maximum shifts to lower temperatures at lower frequencies and to higher temperatures at higher frequencies. Also it should be noted that the values for the almost saturated aqueous NaCl solution is only slightly lower than that for the pure water. Values of $k''$ for the hydrocarbons in most crude oils are less than about 0.05 at the above wavelength, as can be determined from "Tables of Dielectric Dispersion Data for Pure Liquids and Dilute Solutions" by Floyd Buckley et al, Nov. 1958, NTIS PB-188296.

The attenuation coefficients, $\alpha$ for the pure water and the 253 kppm NaCl solution were computed for the temperature range 0° to 60° C. (32° to 140° F.) at a wavelength of 1.267 cm. The attenuation coefficient for the liquid hydrocarbons in crude oils computes to less than 0.0013 cm$^{-1}$ over the same temperature range.

The foregoing assumes that the crude oil does not contain free gas. When the crude oil contains free gas the free gas must be accounted for to determine a correct water in crude content.

Let L be the total microwave beam path, then microwave attenuation of initial value $I_o$ to the value I can be expressed by the following equation:

$$I = I_o \cdot \exp[-\alpha \cdot l_w] \quad (4)$$

where $l_w$ = length of beam in water. However, we have $$l_w = l_L \cdot \eta \quad (5)$$

where
$l_L$ = length of beam in liquid (crude and water)
$\eta$ = water/liquid fraction,
and $$l_L = L \cdot \theta \tag{6}$$

where $\theta$ = fraction of length L which is filled with liquid.

We can now write equation (4) using equations (5) and (6) as follows:

$$I = I_o \cdot \exp[-\alpha \cdot L \cdot \theta \cdot \eta], \tag{7}$$

or $$\theta \cdot \eta = (1/\alpha L) \ln (I_o/I), \tag{7a}$$

$\theta$ is also the average void fraction in the measuring path. This void fraction can be measured e.g. with a gamma ray density gauge as follows.

A gamma ray beam traversing the measuring section of length L is attenuated by the material (gas, water, oil) within this section. This attenuation can be described by equation (5).

$$I_y = I_{oy} \cdot \exp\{-[\mu_g \cdot l_g + \mu_w \cdot l_w + \mu_{oil} \cdot l_{oil}]\}, \tag{8}$$

where $\mu_g$, $\mu_w$, $\mu_{oil}$ are the gamma ray attenuation coefficients per unit length for gas, water and oil, respectively; $l_g$, $l_w$, $l_{oil}$ are the thicknesses of gas, water and oil, respectively, within the path length; $I_{oy}$ is the initial gamma ray intensity, $I_y$ the attenuated gamma ray intensity.

The following relationships between the above parameters $i$ (i.e. g, w, oil), L, $\eta$ and $\theta$ exist.

$$L = l_g + l_w + l_{oil} \tag{9}$$

$$l_L = l_w + l_{oil} = L \cdot \theta \tag{10}$$

$$l_w = l_L \cdot \eta \tag{11}$$

$$l_g = L(1-\theta). \tag{12}$$

Using the relationships of (9) through (12) to substitute for $l_g$, $l_w$ and $l_{oil}$ in equation (8) the following is obtained $$I_y = I_{oy} \exp\{-L[\mu_g + \theta(\mu_{oil} - \mu_g + \eta(\mu_w - \mu_{oil}))]\}, \tag{13}$$

and $$(1/L)[\ln (I_{oy}/I_y)] = \mu_g + \theta[(\mu_{oil} - \mu_g) + \eta(\mu_w - \mu_{oil})], \tag{14}$$

or $$\theta = \{(1/L)[\ln (I_{oy}/I_y)] - \mu_g\} / [(\mu_{oil} - \mu_g) + \eta(\mu_w - \mu_{oil})]. \tag{15}$$

Substituting equation (15) into equation (7a) to eliminate $\theta$ and rearranging terms yields equation (16) for determining $\eta$, the water/liquid ratio, from measured and known parameters $$\eta = [(1/\alpha L) \ln (I_o/I) \cdot (\mu_{oil} - \mu_g)] / [(1/L) \ln (I_{oy}/I_y) - \mu_g - (1/\alpha L)(\mu_w - \mu_{oil}) \cdot \ln (I_o/I)]. \tag{16}$$

In many cases $\mu_w = \mu_{oil} = \mu$ and $\mu_g << \mu$ may be utilized without making large errors, equation (16) then reduces to $$\eta = [(1/\alpha L) \cdot \mu \cdot \ln (I_o/I)] / [(1/L) \ln (I_{oy}/I_y) - \mu_g]. \tag{17}$$

Using again relationships of (9) through (12) the fractional water oil ratio can be calculated from the water/liquid ratio by equation (18)

$$\text{water/oil fraction} = \eta/(1-\eta). \tag{18}$$

Figure 2:
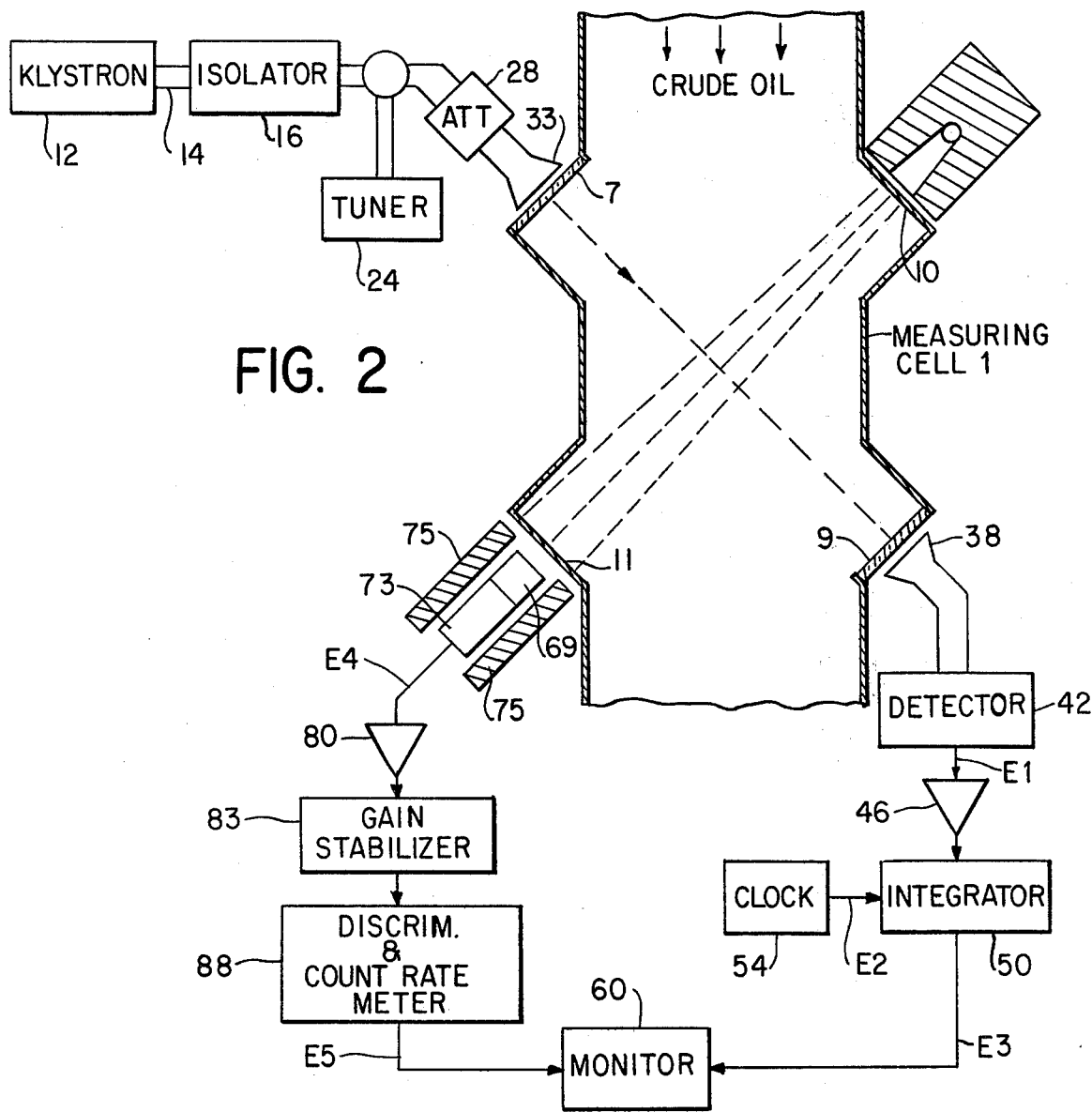
FIG. 2 is a simplified block diagram of a water-in-crude monitor constructed in accordance with the present invention.

Referring now to FIG. 2, oil flowing from a well head enters a measuring cell 1 by way of a pipe (not shown) and leaves cell 1 by way of a pipe (not shown). Cell 1 includes ceramic windows 7, 9 and steel windows 10, 11. A conventional type klystron 12 provides microwave frequency radiation through wave guides 14 to an isolator 16. Isolator 16 stops reflected microwaves from entering klystron 12; a tuner 24 provides a mechanical type tuning for matching the transmission subsystem when isolator 16 provides microwaves to attenuator 28.

Attenuator 28 provides attenuated microwaves to a conventional horn antenna 33 which propagates the microwaves through window 7 and through window 9 to a second horn antenna 38. Horn antenna 38 provides the received microwaves to a microwave detector 42 which in turn provides an electrical signal E1 to an amplifier 46. The amplified signal from amplifier 46 is provided to an integrator 50 receiving pulse E2 from a clock 54 and provides an integrated signal E3 to a monitor 60.

A gamma ray source 65, located in a shield and collimator 67, provides gamma ray beam through window 10 across measuring cell 1 and through window 11. Shield and collimator 67 may be made of lead or tungsten.

A radiation detector 69, which may be a conventional type sodium iodide (thallium activated) crystal detector, detects the gamma radiation passing through window 11 and provides light pulses, corresponding in number and amplitude to the detected gamma radiation, to a photo multiplier tube 73. Detector 69 and photomultiplier tube 73 are surrounded by a shield 75 which prevents the gamma radiation passing through window 11 from escaping from the area. Photomultiplier tube 73 provides electrical pulses on a one-for-one basis with the light pulses from detector 69 to an amplifier 80 where they are amplified and provided to a gain stabilizer 83. Gain stabilizer 83 may be a type manufactured by Hawshaw Chemical Co. as their part No. NA-22AGC Amplifier. Gain stabilizer 83 provides corresponding pulses to a conventional type discriminator and count rate meter 88. Discriminator and count rate meter 88 provides a signal E5, corresponding to the detected radiation, to monitor 60.

Figure 3:
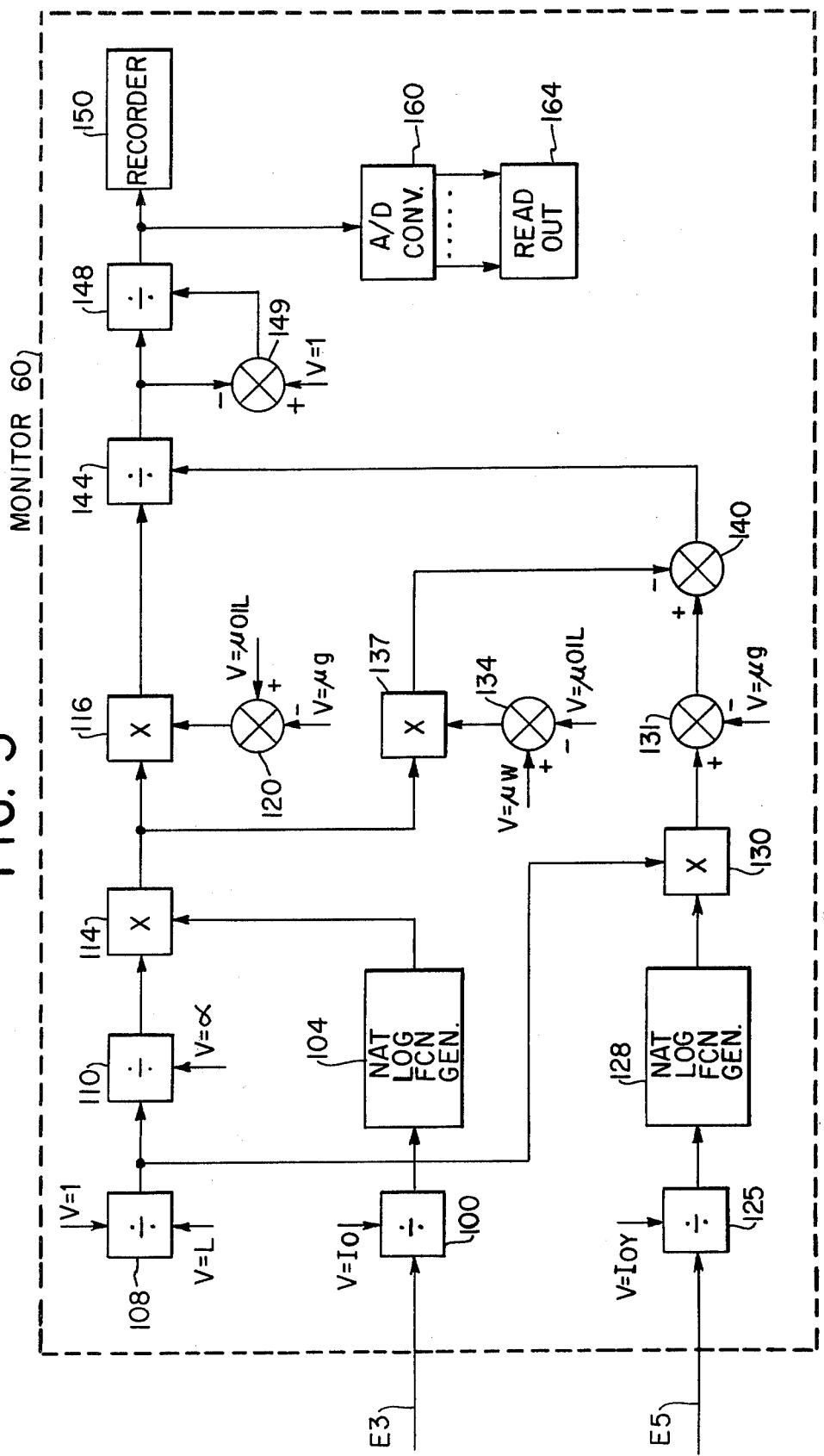
FIG. 3 is a detailed block diagram of the monitor shown in Fig. 2.

Referring now to FIG. 3, signal E3 corresponding to the term I in equation 16 is applied to a divider 100 in monitor 60 where it is divided into a DC voltage corresponding to a value of $I_o$. Divider 100 provides a signal to a natural log function generator 104 which in turn provides a signal corresponding to the term ln ($I_o/I$) in equation 16.

A divider 108 divides a DC voltage corresponding to a value for L, the distance from source 65 to detector 69, into a DC voltage corresponding to a value of 1. Divider 108 divides a signal to another divider 110 where it has a DC voltage corresponding to the attenuation constant $\alpha$ into it to provide a signal. The attenuation constant $\alpha$ may be determined prior to operation by determining $I_o$ with measuring cell 1 empty, then filling measuring cell 1 with water and determining I and solving equation 4 for $\alpha$ knowing the length of the microwave beam in the water. A multiplier 114 multiplies the signals from natural log function generator 104 and divider 110 to provide another signal to a multiplier 116.

Subtracting means 120 subtracts a direct current voltage corresponding to $\mu_g$ from a direct current voltage corresponding to $\mu_{oil}$ to provide a difference signal to multiplier 116 where it is multiplied with the signal from multiplier 114 to provide a product signal. The constants $\mu_g$, $\mu_{oil}$ are determined in the same manner as the dielectric constant by utilizing equation 4, using $I_y$ for I and $I_{oy}$ for $I_o$, and filling the measuring cell 1 with gas of the type encountered in the producing well for the constant $\mu_g$ and then filling measuring cell 1 with oil of the type provided by the well to obtain the constant $\mu_{oil}$.

Signal E5 is applied to a divider 125 where it is divided into a DC voltage corresponding to the term $I_{oy}$ in equation 16. The value of $I_{oy}$ is determined prior to operation by detecting the gamma radiation from source 65 while measuring cell 1 is empty. An output signal from divider 125 is applied to a natural log function generator 128 which provides a signal corresponding to the term ln $(I_{oy}/I_y)$ in equation 16. A multiplier 130 multiplies the signal provided by divider 108 with the signal from natural log function generator 128 to provide a corresponding signal. Subtracting means 131 subtracts the voltage corresponding to $\mu_g$ from the signal provided by multiplier 130 to provide a signal.

Subtracting means 134 subtracts the voltage corresponding to $\mu_{oil}$ from the voltage corresponding to $\mu_w$ to provide a difference signal. A multiplier 137 multiplies the signals from multiplier 114 and subtracting means 134 to provide a product signal which is subtracted from the signal provided by subtracting means 131 by subtracting means 140. A divider 144 divides the signal provided by subtracting means 140 into the signal from multiplier 116 to provide a signal corresponding to the term $\eta$ to a divider 148 and to subtracting means 149.

Subtracting means 149 subtracts the signal provided by divider 144 from the voltage corresponding to the value of 1 to provide a signal which is divided into the signal provided by divider 144 by a divider 148. Divider 148 provides a signal, corresponding to the water to oil fraction, to a recorder 150 and to an analog to digital converter 160. Converter 160 converts the analog signal from divider 148 to digital signals which are provided to readout means 164.

The present invention as hereinbefore described is a water-in-crude monitor that determines the water to oil fraction utilizing microwaves and gamma rays so that water-in-crude oil that contains gas may be monitored.

What is claimed is:

1. A system for measuring the percent quantity of water in crude oil flowing in a pipe line comprising cell means arranged with pipe line so that the crude oil flows through the cell means, microwave transmission means spatially arranged with the cell means for transmitting microwave energy through the crude oil flowing through the cell means, source means spacially related to the cell means for emitting gamma rays through the crude oil flowing through the cell means, receiver means spatially arranged with the cell means for receiving the transmitted energy and for providing a signal corresponding to the received microwave energy, detector means for detecting the gamma rays that passed through the crude oil and providing a corresponding signal, and monitor means connected to the receiver means and to the detector means for providing an indication of the quantity of water in the crude oil.

2. A system as described in claim 1 in which the cell means includes a pair of ceramic windows arranged in the cell means so that the radiant energy is transmitted through one ceramic window and received by the receiver means through the other ceramic window.

3. A system as described in claim 2 in which the transmission means includes klystron means providing microwave output, wave guide means for conducting the microwaves from the klystron means, tuning means for tuning the microwaves, isolator means arranged between the tuning means and the klystron means for preventing feedback of microwaves to the klystron means, means receiving the microwaves for attenuating them, and first antenna means receiving the attenuated microwaves for transmitting the microwave energy through the one ceramic window.

4. A system as described in claim 3 in which the receiver means includes second antenna means arranged with the other ceramic window for receiving the transmitted energy, a detector coupled with the second antenna means provides a signal corresponding to the received microwave energy, an amplifier connected to the detector amplifies the signal from the detector, and integrating means connected to the amplifier and to the indicating means for providing an integrated signal to the monitor means in accordance with the signal from the amplifier.

5. A system as described in claim 4 in which the cell means includes a pair of windows arranged in the cell means so that the gamma rays are transmitted through one window through the cell means and passes through the other window to impinge upon the detector means.

6. A system as described in claim 5 in which the source means includes a source of gamma rays spacially arranged with the cell means so that some of the emitted gamma rays will pass through the one window, and shield means spacially arranged with the gamma ray source for blocking gamma rays emitted by the gamma ray source that do not pass through the one window.

7. A system as described in claim 6 in which the detector means includes pulse means for providing pulses corresponding to gamma radiation impinging on said pulse means, and discriminator and count rate meter means connected to the pulse means for counting pulses from the pulse means related to a predetermined detected gamma ray energy level and providing a signal corresponding thereto.

8. A system as described in claim 7 in which the monitor means includes $\eta$ signal means receiving direct current voltages corresponding to $\alpha$, L, $\mu_{oil}$, $\mu_g$, $\mu_w$, $I_0$, and $I_{0y}$, which are representative of a predetermined attenuation constant, a predetermined length for the path of the gamma rays through the cell means, to the gamma ray attenuation coefficient per unit length for oil, the gamma ray attenuation coefficient per unit length for oil, the gamma ray attenuation coefficient per unit length for gas, the gamma ray attenuation coefficient per unit length for water, the initial microwave energy and the initial gamma ray intensity, and connected to the integrating means and the discriminator and count rate means for providing a signal corresponding to the water/liquid fraction $\eta$ and in accordance with the received voltages the signals from the integrating means and the discriminator and count rate means and the following equation:

$$\eta = \{(1/\alpha L) \ln (I_o/I)(\mu_{oil} - \mu_g)\}/\{(1/L) \ln (I_{oy}/I_y) - \mu_g - (1/\alpha L)(\mu_w - \mu_{oil}) \ln (I_o/I)\}$$

and, output means connected to the $\eta$ signal means and receiving a DC voltage corresponding to a value of 1 for providing a signal corresponding to the water/oil fraction in accordance with the $\eta$ signal and the received voltage and the following equation:

$$\text{water/oil} = \eta/(1-\eta).$$

9. A system as described in claim 8 in which the monitor means also includes recorder means connected to the output means for recording the signal from the output means.

10. A system as described in claim 8 or 9 in which the monitor means includes readout means connected to the output means for providing a readout of the water/oil fraction in accordance with the output signal.

* * * * *